United States Patent [19]

Bergstrom et al.

[11] 4,267,171
[45] May 12, 1981

[54] C-5 SUBSTITUTED CYTOSINE NUCLEOSIDES

[75] Inventors: Donald E. Bergstrom, Davis; Jerry L. Ruth, Encinitas, both of Calif.

[73] Assignee: The Regents of the University of California, Berkeley, Calif.

[21] Appl. No.: 53,943

[22] Filed: Jul. 2, 1979

[51] Int. Cl.$^3$ .................. A61K 31/70; C07H 17/00
[52] U.S. Cl. ................................. 424/180; 536/23
[58] Field of Search .................... 536/23; 424/180

[56] References Cited

U.S. PATENT DOCUMENTS

| | | | |
|---|---|---|---|
| 3,282,921 | 11/1966 | Verheyden et al. | 536/23 |
| 3,376,283 | 4/1968 | Hunter | 536/23 |
| 3,856,777 | 12/1974 | Ishido et al. | 536/23 |
| 3,891,623 | 6/1975 | Vorbrüggen et al. | 536/23 |
| 3,998,807 | 12/1976 | Moffatt | 536/23 |

OTHER PUBLICATIONS

Bergstrom, D. E., et al., J. Carbohydrates, Nucleosides, Nucleotides, vol. 4, 257–269 (1977).
Ruth, J. L., et al., J. Org. Chem., vol. 43, 2870–2876 (1978).
Bergstrom, D. E., et al., JACS, vol. 100, 8106–8112 (1978).
Wataya, Y., et al., J. of Medicinal Chem., vol. 22, 339 (1979).
Bergstrom et al., J. Am. Chem. Soc., vol. 98, 1587 (1976).
Kulikowski et al., J. Med. Chem., vol. 17, 269 (1974).

*Primary Examiner*—Johnnie R. Brown
*Assistant Examiner*—Blondel Hazel
*Attorney, Agent, or Firm*—Bertram I. Rowland

[57] ABSTRACT

C-5 Substituted cytosine nucleosides wherein the C-5 substituent is substituted alkyl, alkenyl or substituted alkenyl; and the pharmaceutically acceptable acid addition salts thereof, are useful as antiviral agents. A novel process for the preparation of the subject compounds is also disclosed.

7 Claims, No Drawings

C-5 SUBSTITUTED CYTOSINE NUCLEOSIDES

The invention described herein was made in the course of, or under, a grant from the National Cancer Institute.

The present invention relates to the chemistry of nucleosides and, more particularly, is directed to novel C-5 substituted cytosine nucleosides, a novel method for the preparation of these compounds and the use of such compounds as antiviral agents.

The subject compounds of the present invention can be represented by the following generic formula:

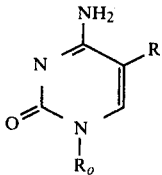
(I)

wherein $R_0$ is $\beta$-D-ribofuranosyl, $\beta$-D-2-deoxyribofuranosyl or $\beta$-D-arabinofuranosyl and R is selected from the group consisting of

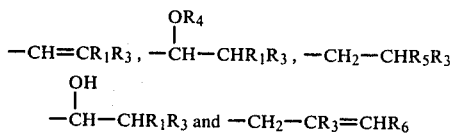

wherein $R_1$ is hydrogen, $C_nH_{2n+1}$ where n is 1 to 6 or $C_nH_{2n}Y$ where n is 0 to 2 and Y is hydroxymethyl, cyanomethyl, trifluoromethyl, penyl, carbmethoxy, —C(O)$R_2$ or —CH$_2$C(O)N($R_2$)$_2$ where $R_2$ is $C_{1-4}$ lower alkyl; $R_3$ is hydrogen or methyl; $R_4$ is $C_{1-4}$ lower alkyl; $R_5$ is $C_nH_{2n}Y$ where n is 0 to 2 and Y is as previously defined; and $R_6$ is hydrogen or $C_nH_{2n+1}$ where n is 1 to 3.

The subject compounds of formula (I) include the pharmaceutically acceptable acid addition salts thereof. Acids which may be used to prepare the salts are those containing non-toxic anions and include for example, inorganic acids such as hydrochloric acid, sulfuric acid, phosphoric acid and the like and organic acids such as acetic acid, citric acid, tartaric acid, oxalic acid, succinic acid, maleic acid, gluconic acid and the like.

Compounds embraced by generic formula (I) can be represented subgenerically as:

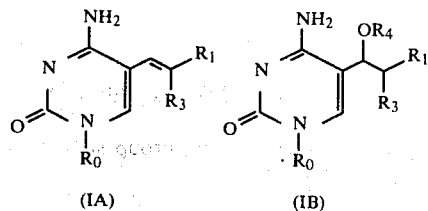

(IA)   (IB)

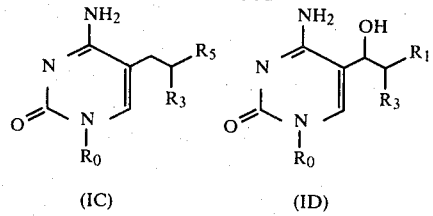

(IC)   (ID)

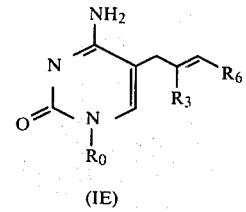

(IE)

wherein $R_0$, $R_1$, $R_3$, $R_4$, $R_5$ and $R_6$ are as previously defined.

Preferred compounds embraced by subgeneric formulas (IA) to (IE) are those wherein $R_0$ is $\beta$-D-2-deoxyribofuranosyl or $\beta$-D-arabinofuranosyl.

Preferred compounds within the group described in the previous paragraph are:

1. Compounds of formula (IA) wherein $R_1$ is hydrogen or $C_nH_{2n}Y$ and Y is trifluoromethyl, cyanomethyl or carbmethoxy. Particularly preferred compounds within the foregoing group are those wherein $R_1$ is hydrogen, trifluoromethyl, cyanomethyl or carbmethoxy. Especially preferred compounds within the foregoing group are those wherein:
   (a) $R_1$ is hydrogen and $R_3$ is methyl;
   (b) $R_1$ and $R_3$ are hydrogen;
   (c) $R_1$ is trifluoromethyl and $R_3$ is hydrogen; and
   (d) $R_1$ is cyanomethyl and $R_3$ is hydrogen.
2. Compounds of formula (IC) wherein $R_5$ is trifluoromethyl, cyanomethyl or carbmethoxy.
3. Compounds of formula (IE) wherein:
   (a) $R_3$ and $R_6$ are hydrogen; and
   (b) One of $R_3$ and $R_6$ is methyl and the other is hydrogen.

The subject compounds of formula (I) are particularly useful as antiviral agents in treatment of numerous mammalian viral infections such as herpes simplex type 1 and type 2, vaccinia, cytomegalovirus and the like. In addition, the subject compounds are useful as antineoplastic agents and also produce metabolic deficiencies in biological systems such as in vitro and in vivo inhibition of enzymes requisite for DNA and/or RNA synthesis, or are precursors for compounds which produce such deficiencies.

Accordingly, a further aspect of the present invention relates to pharmaceutical compositions which comprise the subject compounds of formula (I) or pharmaceutically acceptable acid addition salts thereof in combination with a pharmaceutically acceptable non-toxic carrier.

Useful pharmaceutical carriers for the preparation of the compositions hereof can be solids, liquids, or gases. Thus, the compositions can take the form of tablets, pills, capsules, powders, sustained release formulations, solutions, suspensions, elixirs, aerosols, and the like. The carriers can be selected from the various oils including those of petroleum, animal, vegetable or synthetic origin. Specific oils that may be employed include peanut oil, soybean oil, mineral oil, sesame oil and the like.

Water, saline, aqueous dextrose and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, and the like. Suitable pharmaceutical carriers and their formulation are described in "Remingtons Pharmaceutical Sciences" by E. W. Martin. Such compositions will, in any event, contain an effective amount of the active compound together with a suitable amount of carrier so as to prepare the correct dosage form for proper administration to the host.

The present invention also relates to a method of treating a virus infection in a host subject afflicted with same, which method comprises administering to the host subject an effective amount of a compound of the present invention or a suitable composition containing same.

In general, it is expedient to administer the subject compounds in amounts of between about 1 and 100 mg/kg body weight per day or other regular course of treatment (preferably between 5 and 50 mg/kg body weight per day) distributed in several individual doses in order to achieve effective results. The subject compounds and compositions may be administered by conventional methods, e.g., topically, orally, parenterally and the like, and in any form suitable for the administration mode, i.e., isotonic solutions, suspensions, tablets, capsules and the like.

The exact dosage and regimen for administration of the compounds and compositions disclosed herein will necessarily be dependent upon the needs of the host subject being treated, the type of virus involved and the compound employed. In any event the compositions to be administered will contain a quantity of the subject compound in an amount effective for relief of the specific condition being treated.

In addition to manifesting a high order of activity against various viruses, the compounds of the present invention are relatively non-cytotoxic. For example, when tested against a prototype strain (HSV-1), the therapeutic index is usually greater than 100. Comparable compounds which have been suggested as antiviral agents do not combine this high order of activity with low toxicity (e.g., compounds such as 1-$\beta$-D-arabinofuranosylcytosine have a therapeutic index in HSV-1 approaching unity).

DETAILED DESCRIPTION

The present invention, in a still further aspect, is directed to methods for the preparation of the subject compounds, which methods can be schematically represented as follows:

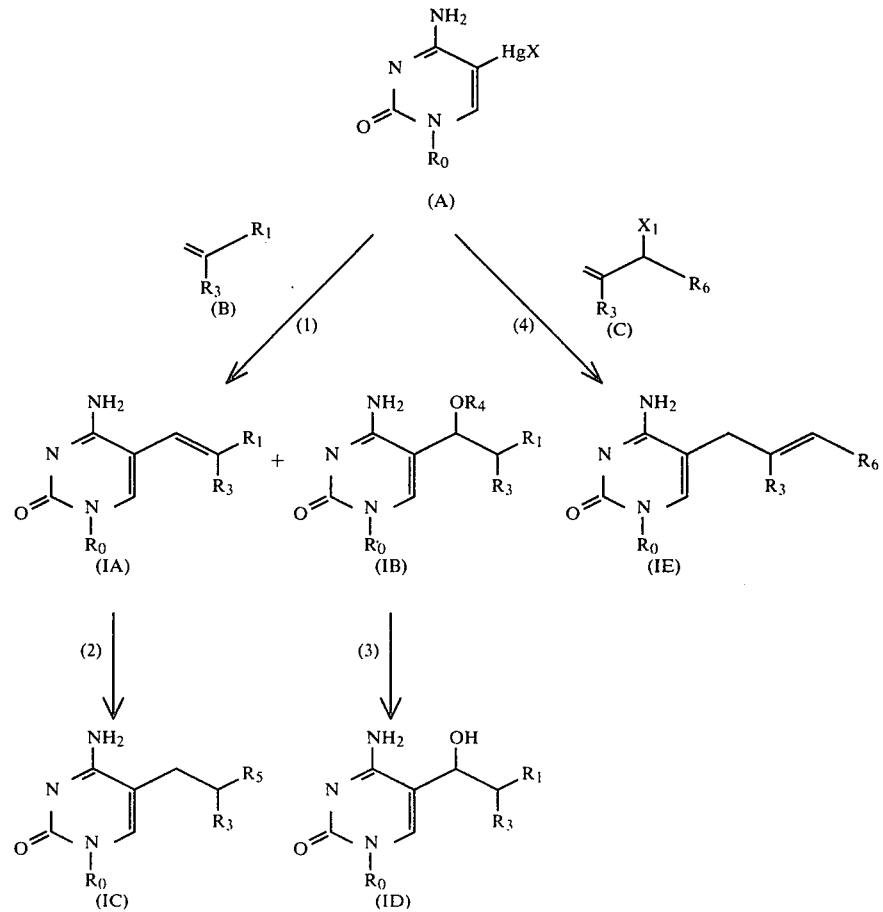

wherein:

X is a conventional ligand such as chloro, acetoxy, or trifluoroacetoxy;

$X_1$ is a conventional leaving group such as chloro, acetoxy, or hydroxy;

$R_0$ is $\beta$-D-ribofuranosyl, $\beta$-D-2-deoxyribofuranosyl or $\beta$-D-arabinofuranosyl;

$R_1$ is hydrogen, $C_nH_{2n+1}$ wherein n is 1 to 6 or $C_nH_{2n}Y$ wherein n is 0 to 2 and Y is hydroxymethyl, cyanomethyl, trifluoromethyl, phenyl, carbmethoxy, $-C(O)R_2$ or $-CH_2C(O)N(R_2)_2$ wherein $R_2$ is $C_{1-4}$ lower alkyl;

$R_3$ is hydrogen or methyl;

$R_4$ is $C_{1-4}$ lower alkyl;

$R_5$ is $C_nH_{2n}Y$ wherein n is 0 to 2 and Y is as previously defined; and $R_6$ is hydrogen or $C_nH_{2n+1}$ where n is 1 to 3.

Reaction (1) in the above schematic diagram can be conveniently effected by treating a C-5 mercurated cytosine nucleoside (A) with a terminally unsaturated compound of formula (B) in the presence of an inorganic or organic palladium (II) complex using mole ratios of (A) to (B) in the range of about from 1:1 to 1:20, preferably about 1:7 to 1:12, and employing the palladium complex (1) in slight molar excess of (A) i.e., 1.1 to 2.5 equivalents, or (2) in catalytic amounts, i.e., 0.01 to 0.05 equivalents, if a suitable reoxidant such as, for example, copper (II) chloride is included. The reaction is carried out in a suitable solvent, preferably under an inert atmosphere, at temperatures in the range of 0° C. to 60° C., preferably at about room temperature, for about from 1 to 120 hours, preferably about 3 to 24 hours. Suitable solvents include, for example, methanol, isopropanol, N,N-dimethylformamide, acetonitrile, methyl formate, water and the like, and mixtures thereof. When the solvent comprises a lower alkanol (e.g., methanol, isopropanol, etc.), the reaction is productive of both (IA) and (IB) which may be separated chromatographically. Use of a non-alkanolic solvent is productive of (IA) only. Suitable palladium complexes that may be employed include, for example, lithium tetrachloropalladate ($Li_2PdCl_4$) and lithium trichloropalladate ($LiPdCl_3$) as well as other alkaline or alkaline earth metal palladates; palladium (II) chloride, palladium (II) acetate and other complexes of palladium (II) with conventional ligands. The preferred palladium complex is $Li_2PdCl_4$.

The starting materials of formula (A) are known compounds and can be prepared by procedures described by Bergstrom et.al. in *J. Carbohydrates-Nucleosides-Nucleotides*, 4(5), 257–269 (1977) and references incorporated therein or by obvious modification of such procedures. The starting materials of formula (B) are commercially available or can be prepared by conventional synthetic routes.

Reaction (2), reduction of carbon-carbon double bonds in the C-5 substituent of compounds of formula (IA) wherein $R_1$ is $C_nH_{2n}Y$ can be effected by treatment with hydrogen in a suitable solvent in the presence of a reductive catalyst. Typically the reaction is conducted at room temperature utilizing from about 1 to 3 atmospheres of hydrogen pressure for about from 0.5 to 48 hours, preferably 0.5 to 6 hours. Suitable solvents that may be used include, for example, methanol water and the like. Suitable reductive catalysts which can be used include, for example, palladium on carbon and other catalysts of similar reductive activity.

Reaction (3), ether hydrolysis at the α-position of the C-5 substituent, can be effected by treatment of (IB) with aqueous inorganic acid at room temperature for about from 2 to 150 hours, preferably 24 to 48 hours. Suitable acids that may be used include, for example, HCl, $H_2SO_4$, $HNO_3$ and the like. The concentration of acid employed is typically 0.001 to 0.5 M, preferably 0.02 to 0.05 M.

Reaction (4) can be effected by treating a C-5 mercurated cytosine nucleoside (A) with a terminally unsaturated compound of formula (C) in the presence of a palladium (II) complex in the manner previously set forth in the description of Reaction (1).

It is generally preferred that the respective products of each reaction described hereinabove, be separated and/or isolated prior to use as a starting material for a subsequent reaction. Separation and isolation can be effected by any suitable purification procedure such as, for example, evaporation, filtration crystallization, column chromatography, thin layer chromatography, etc. Specific illustrations of typical separation and isolation procedures can be had by reference to the appropriate examples described hereinbelow; however, other equivalent separation procedures can, of course, also be used. Also, it should be appreciated that where typical reaction conditions (e.g. temperatures, mole ratios, reaction times) have been given that conditions both above and below these ranges can also be used, though generally less conveniently.

Certain compounds embraced by formulas (IA), (IB), (IC) and (ID) contain C-5 substituents terminated with $-C(O)OCH_3$ or $-C\equiv N$. These groups may be readily transformed into other functional groups by conventional methods, such as, for example, transesterification, saponification, neutralization, aminolysis, reduction, hydration and the like. For example, $-C(O)OCH_3$ can be converted to a different ester moiety, the free acid, acid salt, or an amide function by appropriate treatment. Likewise, $-C\equiv N$ can be converted to an amine or amide moiety.

The pharmaceutically acceptable acid addition salts of the subject compounds of formula (I) may be readily prepared by treatment of a C-5 substituted cytosine nucleoside of formula (IA), (IB), (IC), (ID), or (IE), with a suitable acid in aqueous media followed by evaporation of the solvent, for example, by freeze drying.

DEFINITIONS

The following terms, as used hereinabove and below, have the following meanings unless expressly stated to the contrary.

The term $C_nH_{2n+1}$ refers to a saturated, branched or unbranched, acyclic hydrocarbon group containing 1 to 6 or 1 to 3 carbon atoms. Representative examples of such groups are methyl, ethyl n-butyl, isobutyl, tert-butyl, n-pentyl, isopentyl, n-hexyl, and the like.

The term carbmethoxy refers to a functional group having the formula

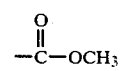

The numbering system and nomenclature used to define and describe the subject compounds of the present invention are those conventionally employed in the art. For example, the numbering system for cytosine nucleosides is denoted thus:

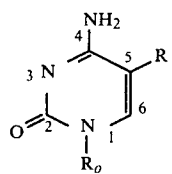

(I)

The point of attachment of the cytosine ring to the C-5 substituent is designated by prefacing "-yl" by the number of the carbon in the carbon skeleton of the substituent. For example, 5-(prop-2-en-1-yl)cytidine is structurally denoted as follows:

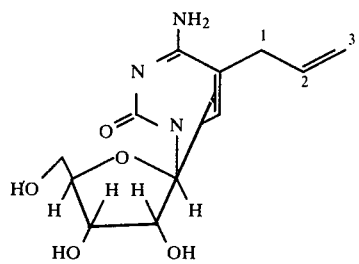

The numbering of the carbon chain in the C-5 substituent is such that the carbon attached to the cytosine nucleus is designed as the first carbon. For example, 5-(4-carbmethoxy-2-methylbut-1-en-1-yl)-1-$\beta$-D-arabinofuranosylcytosine is structurally denoted as:

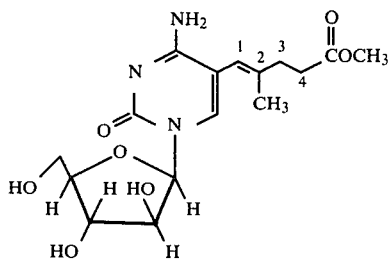

A further understanding of this invention can be had from the following non-limiting preparations and examples wherein: (1) proton magnetic resonance spectra ($^1$H NMR) are determined at 60 or 100 mHz, the signals are defined as singlet (s), doublet (d), triplet (t), multiplet (m), combinations of these (e.g., dd is doublet of doublets), and descriptive terms such as broad or narrow (locations of absorptions are in ppm downfield from currently employed standards); (2) ultraviolet spectra (UV) are determined, the wavelengths of maximum absorption ($\lambda_{max}$ H$_2$O) and of minimum absorption ($\lambda_{min}$ H$_2$O) are given in nanometers (nm) for neutral aqueous solutions of the compund; and (3) elemental analyses are determined, the empirical formula of the compound is given with the calculated mass ratios as % of total (e.g., C, 50.88 indicates a calculated 50.88% carbon by weight) and the experimental % by mass are included in like form.

DESCRIPTIONS OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLES I–VIII refer to Reaction (1).

EXAMPLE I 5-(Propen-1-yl)cytidine and 5-(1-methoxyprop-1-yl)cytidine

5-Chloromercuricytidine (1.4 g, 3 mmol) and 33 ml of 0.1 N Li$_2$PdCl$_4$ in methanol are stirred under two atmospheres of propylene for about 12 hours at room temperature. The reaction is then filtered, the filtrate treated with hydrogen sulfide for about one minute, and the resulting insoluble metal sulfides filtered out. Evaporation of the methanolic filtrate to near dryness and column chromatography of the products on a molecular exclusion resin (such as Bio-Gel P-2) eluting with water yields two major products. Independent lyophilization of the aqueous solutions affords 5-(propen-1-yl)cytidine and 5-(1-methoxy-prop-1-yl)cytidine as white amorphous solids.

Repeating the above procedure using 0.2 equivalents of Li$_2$PdCl$_4$ and 2.1 euivalents of CuCl$_2$ is also productive of 5-(propen-1-yl)cytidine and 5-(1-methoxyprop-1-yl)cytidine.

5-(Propen-1-yl)cytidine decomposes upon heating; $^1$H NMR (D$_2$O) $\delta$:7.9 (S,1), 6.1 (narrow m,2), 5.9 (narrow m,1) 4.2 (m,3), 3.9 (narrow m,2), 1.8 (d,3,J=5 Hz); UV $\lambda_{max}^{H2O}$ 233 nm ($\epsilon$13000), 288 nm ($\epsilon$5100); $\lambda_{min}^{H2O}$ 271 nm ($\epsilon$4000).

EXAMPLE II

Repeating the procedure of Example I but replacing propylene with:
ethylene,
1-butene,
1-pentene,
1-hexene,
1-heptene,
1-octene,
2-methylpropene,
2-methyl-1-pentene, or
2,4-dimethyl-1-pentene
is productive of the following 5-alkenylcytidines of formula (IA), i.e.
5-ethenylcytidine,
5-(but-1-en-1-yl)cytidine,
5-(pent-1-en-1-yl)cytidine,
5-(hex-1-en-1-yl)cytidine,
5-(hept-1-en-1-yl)cytidine,
5-(oct-1-en-1-yl)cytidine,
5-(2-methylpropen-1-yl)cytidine,
5-(2-methylpent-1-en-1-yl)cytidine and
5-(2,4-dimethylpent-1-en-1-yl)cytidine
as well as the corresponding 5-1-(1-methoxyalkyl)cytidines of formula (IB)).

Similarly, the use of other alkanolic solvents (e.g. ethanol, isopropanel, etc.) is productive of the corresponding 5-(1-alkoxyalkyl)cytidines wherein alkoxy is other than methoxy.

EXAMPLE III

Repeating the procedures of Examples I and II but replacing 5-chloromercuricytidine with 5-chloromercuri-2'-deoxycytidine is productive of the following 5-alkenyl-2'-deoxycytidines of formula (IA), i.e.
5-(propen-1-yl)-2'-deoxycytidine,
5-(ethenyl)-2'-deoxycytidine,
5-(but-1-en-1-yl)-2'-deoxycytidine,
5-(pent-1-en-1-yl)-2'-deoxycytidine, 5-(hex-1-en-1-yl)-2'-deoxycytidine,
5-(hept-1-en-1-yl)-2'-deoxycytidine,
5-(oct-1-en-1-yl)-2'-deoxycytidine,
5-(2-methylpropen-1-yl)-2'-deoxycytidine,
5-(2-methylpent-1-en-1-yl)-2'-deoxycytidine and
5-(2,4-dimethylpent-1-en-1-yl)-2'-deoxycytidine
as well as the corresponding 5-(1-methoxyalkyl)-2'-deoxycytidines of formula (IB). Similarly, the use of other alkanolic solvents (e.g., ethanol, isopropanol, etc.) is productive of the corresponding 5-(1-alkoxyalkyl)-2'-deoxycytidines wherein alkoxy is other than methoxy.

EXAMPLE IV

Repeating the procedures of Examples I and II but replacing 5-chloromercuricytidine with 5-chloromercuri-1-β-D-arabinofuranosylcytosine is productive of the following C-5 alkenyl-1-β-D-arabinofuranosylcytosines of formula (IA), i.e.:
5-(propen-1-yl)-1-β-D-arabinofuranosylcytosine,
5-(ethenyl)-1-β-D-arabinofuranosylcytosine,
5-(but-1-en-1-yl)-1-β-D-arabinofuranosylcytosine,
5-(pent-1-en-1-yl)-1-β-D-arabinofuranosylcytosine,
5-(hex-1-en-1-yl)-1-β-D-arabinofuranosylcytosine,
5-(hept-1-en-1-yl)-1-β-D-arabinofuranosylcytosine,
5-(oct-1-en-1-yl)-1-β-D-arabinofuranosylcytosine,
5-(2-methylpropen-1-yl)-1-β-D-arabinofuranosylcytosine,
5-(2-methylpent-1-en-1-yl)-1-β-D-arabinofuranosylcytosine
and
5-(2,4-dimethylpent-1-en-1-yl)-1-β-D-arabinofuranosylcytosine
as well as the corresponding 5-(1-methoxyalkyl)-1-β-D-arabinofuranosylcytosines of formula (IB). Similarly, by employing other alkanoic solvents the analogous 5-(1-alkoxyalkyl)-1-β-D-arabinofuranosylcytosines are produced wherein alkoxy is other than methoxy.

EXAMPLE V 5-(2-Carbmethoxyethenyl)cytidine and
5-(2-Carbmethoxy-1-methoxyethyl)cytidine 5-Chloromercuricytidine (0.96 g, 2 mmol), methyl acrylate (1.8 ml, 20 mmol), and 20 ml of 0.1 N $Li_2PdCl_4$ in methanol are stirred at room temperature for about 12 hours under an inert atmosphere. The resulting black suspension is then filtered. The filtrate is treated with hydrogen sulfide for about one minute, and the resulting insoluble metal sulfides are filtered out. Evaporation of the methanolic filtrate to near dryness and column chromatography on a molecular exclution resin (such as Bio-Gel P-2) eluting with water gives 5-(2-carbmethoxyethenyl)cytidine and 5-(2-carbmethoxy-1-methoxyethyl)cytidine as amorphous solids. Recrystallization of 5-(2-carbmethoxyethenyl)cytidine from water affords analytically pure white crystals; m.p. 220°–221° C. with decomposition; $^1$H NMR (DMSO-$d_6$+1% $D_2O$) δ: 8.7 (s, 1), 7.6 (d, 1, J=16 $H_z$), 6.3 (d, 1, J=16 $H_z$), 5.8 (broad s, 1), 4.1–3.8 (overlapping m, 5), 3.7 (broad s, 3); UV $\lambda_{max}^{H2O}$ 273, 309 nm.

Analysis calculated for $C_{13}H_{17}O_7N_3$: C, 47.71, H 5.24, N 12.84; found, C, 47.65, H 5.23, N 12.79.

EXAMPLE VI

Repeating the procedure of Example V but replacing methyl acrylate with:
methyl methacrylate,
methyl 4-methyl-4-pentenoate,
allyl cyanide,
4-methyl-4-pentenenitrile styrene,
4-phenyl-1-butene,
4-hydroxy-1-butene,
5-hydroxy-2-methyl-1-pentene,
methylvinylketone,
methallylpropylketone,
N,N,3-trimethyl-3-butenamide,
N,N-dibutyl-4-pentenamide,
3,3,3-trifluoropropene, or
4,4,4-trifluoro-1-butene
is productive of the following C-5 substituted cytidines of formula (IA), i.e.,
5-(2-carbmethoxy-2-methylethen-1-yl)cytidine,
5-(4-carbmethoxy-2-methylbut-1-en-1-yl)cytidine,
5-(3-cyanopropen-1-yl)cytidine,
5-(4-cyano-2-methylbut-1-en-1-yl)cytidine,
5-(2-phenylethenyl)cytidine,
5-(4-phenylbut-1-en-1-yl)cytidine,
5-(4-hydroxybut-1-en-1-yl)cytidine,
5-(5-hydroxy-2-methylpent-1-en-1-yl)cytidine,
5-(3-oxobut-1-en-1-yl)cytidine,
5-(2-methyl-4-oxohept-1-en-1-yl)cytidine,
5-[2-methyl-3-(N,N-dimethylamido)propen-1-yl]cytidine
5-[4-(N,N-dibutylamido)but-1-en-1-yl]cytidine
5-(3,3,3-trifluoropropen-1-yl)cytidine, and
5-(4,4,4-trifluorobut-1-en-1-yl)cytidine,
as well as the corresponding α-methoxy C-5 substituted cytidines of formula (IB). Similarly, by employing other alkanolic solvents, the corresponding α-alkoxy C-5 substituted cytidines are produced wherein alkoxy is other than methoxy.

EXAMPLE VII

Repeating the procedures of Examples V and VI but replacing 5-chloromercuricytidine with 5-chloromercuri-2'-deoxycytidine is productive of the following C-5 substituted 2'-deoxycytidines of formula (IA), i.e.,
5-(2-carbmethoxyethenyl)-2'-deoxycytidine,
5-(2-carbmethoxy-2-methylethen-1-yl)-2'-deoxycytidine,
5-(4-carbmethoxy-2-methylbut-1-en-1-yl)-2'-deoxycytidine,
5-(3-cyanopropen-1-yl)-2'-deoxycytidine,
5-(4-cyano-2-methylbut-1-en-1-yl)-2'-deoxycytidine,
5-(2-phenylethenyl)-2'-deoxycytidine,
5-(4-phenylbut-1-en-1-yl)-2'-deoxycytidine,
5-(4-hydroxybut-1-en-1-yl)-2'-deoxycytidine,
5-(5-hydroxy-2-methylpent-1-en-1-yl)-2'-deoxycytidine,
5-(3-oxobut-1-en-1-yl)-2'-deoxycytidine,
5-(2-methyl-4-oxohept-1-en-1-yl)-2'-deoxycytidine,
5-[2-methyl-3-(N,N-dimethylamido)propen-1-yl]-2'-deoxycytidine,
5-[4-N,N-dibutylamido)but-1-en-1-yl]-deoxycytidine,
5-(3,3,3-trifluoropropen-1-yl)-2'-deoxycytidine, and
5-(4,4,4-trifluorobut-1-en-1-yl)-2'-deoxycytidine,
as well as the corresponding α-methoxy C-5 substituted 2'-deoxycytidines of formula (IB). Similarly, by employing other alkanoic solvents, the corresponding α-alkoxy C-5 substituted 2'-deoxycytidines are produced wherein alkoxy is other than methoxy.

EXAMPLE VIII

Repeating the procedure of Examples V and VI but replacing 5-chloromercuricytidine with 5-chloromercuri-1-β-D-arabinofuranosylcytosine is productive of the following C-5 substituted 1-β-D-arabinofuranosylcytosines of formula (IA), i.e., 5-(2-carbmethoxyethenyl)-1-β-D-arabinofuranosylcytosine,
5-(2-carbmethoxy-2-methylethen-1-yl)-1-β-D-arabinofuranosylcytosine,
5-(4-carbmethoxy-2-methylbut-1-en-1-yl)-1-β-D-arabinofuranosylcytosine,
5-(3-cyanopropen-1-yl)-1-β-D-arabinofuranosylcytosine,
5-(4-cyano-2-methylbut-1-en-1-yl)-1-β-D-arabinofuranosylcytosine,
5-(2-phenylethenyl)-1-β-D-arabinofuranosylcytosine,
5-(4-phenylbut-1-en-1-yl)-1-β-D-arabinofuranosylcytosine,
5-(4-hydroxybut-1-en-1-yl)-1-β-D-arabinofuranosylcytosine,
5-(5-hydroxy-2-methylpent-1-en-1-yl)-1-β-D-arabinofuranosylcytosine,
5-(3-oxobut-1-en-1-yl)-1-β-D-arabinofuranosylcytosine,
5-(2-methyl-4-oxohept-1-en-1-yl)-1-β-D-arabinofuranosylcytosine,
5-[2-methyl-3-(N,N-dimethylamido)propen-1-yl]-1-β-D-arabinofuranosylcytosine,
5[4-(N,N-dibutylamido)but-1-en-1-yl]-1-β-D-arabinofuranosylcytosine,
5-(3,3,3-trifluoropropen-1-yl)-1-β-D-arabinofuranosylcytosine,
and
5-(4,4,4-trifluorobut-1-en-1-yl)-1-β-D-arabinofuranosylcytosine,
as well as the corresponding α-methoxy C-5 substituted 1-β-D-arabinofuranosylcytosines of formula (IB). Similarly, by employing other alkanoic solvents the corresponding α-alkoxy C-5 substituted 1-β-D-arabinofuranosylcytosines are produced wherein alkoxy is other than methoxy.

Examples IX to XII refer to Reaction (2).

EXAMPLE IX

5-(3-cyanoprop-1-yl)cytidine

To a solution of 5-(3-cyanopropen-1-yl)cytidine (0.73 mmol) and 20 ml methanol in a 250 ml hydrogenation flask is added 25 mg of 10% Pd/C. The system is evacuated, repressurized with two atmospheres hydrogen gas and then stirred at room temperature. After about two hours, the system is evacuated and the resulting black suspension removed by filtration. The colorless methanolic filtrate is evaporated to dryness affording a white amorphous solid. Recrystallization of the solid from acetonitrile or water, or column chromatography on molecular exclusion resin (such as Bio-Gel P-2) gives 5-(3-cyanoprop-1-yl)cytidine as a white amorphous solid; decomposes upon heating; UV $\lambda_{max}^{H_2O}$ 278 nm ($\epsilon$8400), $\lambda_{min}^{H_2O}$ 254 nm ($\epsilon$4700); $^1$H NMR (D$_2$O) δ:7.72 (s,1), 5.95 (narrow m,1), 4.3 (m,3), 3.92 (narrow m,2), 2.3 (broad m,4), 1.5 (m,2).

EXAMPLE X

Repeating the procedure of Example IX but replacing 5-(3-cyanopropen-1-yl)cytidine with the 5-substituted cytidines of formula (IA) enumerated in Examples V and VI is productive of the following 5-substituted cytidines of formula (IC), i.e.
5-(2-carbmethoxyethyl)cytidine,
5-(2-carbmethoxy-2-methylethyl)cytidine,
5-(4-carbmethoxy-2-methylbut-1-yl)cytidine,
5-(4-cyano-2-methylbut-1-yl)cytidine,
5-(2-phenyleth-1-yl)cytidine,
5-(4-phenylbut-1-yl)cytidine,
5-(4-hydroxybut-1-yl)cytidine,
5-(5-hydroxy-2-methylpent-1-yl)cytidine,
5-(3-oxobut-1-yl)cytidine,
5-(2-methyl-4-oxohept-1-yl)cytidine,
5-[2-methyl-3-(N,N-dimethylamido)prop-1-yl]cytidine,
5-[4-(N,N-dibutylamido)but-1-yl]cytidine,
5-(3,3,3-trifluoroprop-1-yl)cytidine, and
5-(4,4,4-trifluorobut-1-yl)cytidine.

EXAMPLE XI

Repeating the procedure of Example IX, but replacing 5-(3-cyanopropen-1-yl)cytidine with the 5-substituted 2'-deoxycytidines of formula (IA) recited in Example VII is productive of the following 5-substituted 2'-deoxycytidines of formula (IC), i.e.
5-(3-cyanoprop-1-yl)-2'-deoxycytidine,
5-(2-carbmethoxyethyl)-2'-deoxycytidine,
5-(2-carbmethoxy-2-methylethyl)-2'-deoxycytidine,
5-(4-carbmethoxy-2-methylbut-1-yl)-2'-deoxycytidine,
5-(4-cyano-2-methylbut-1-yl)-2'-deoxycytidine,
5-(2-phenyleth-1-yl)-2'-deoxycytidine,
5-(4-phenylbut-1-yl)-2'-deoxycytidine,
5-(4-hydroxybut-1-yl)-2'-deoxycytidine,
5-(5-hydroxy-2-methylpent-1-yl)-2'-deoxycytidine,
5-(3-oxobut-1-yl)-2'-deoxycytidine,
5-(2-methyl-4-oxohept-1-yl)-2'-deoxycytidine
5-[2-methyl-3-(N,N-dimethylamido)prop-1-yl]-2'-deoxycytidine,
5-[4-(N,N-dibutylamido)but-1-yl]-2'-deoxycytidine,
5-(3,3,3-trifluoroprop-1-yl)-2'-deoxycytidine, and
5-(4,4,4-trifluorobut-1-yl)-2'-deoxycytidine

EXAMPLE XII

Repeating the procedure of Example IX, but replacing 5-(3-cyanopropen-1-yl)cytidine with the 5-substituted 1-β-D-arabinofuranosylcytosines of formula (IA) recited in Example VIII is productive of the following 5-substituted 1-β-D-arabinofuranosylcytosines of formula (IC), i.e.
5-(3-cyanoprop-1-yl)-1-β-D-arabinofuranosylcytosine,
5-(2-carbmethoxyethyl-1-β-D-arabinofuranosylcytosine,
5-(2-carbmethoxy-2-methylethyl)-1-β-D-arabinofuranosylcytosine,
5-(4-carbmethoxy-2-methylbut-1-yl)-1-β-D-arabinofuranosylcytosine,
5-(4-cyano-2-methyl-but-1-yl)-1-β-D-arabinofuranosylcytosine,
5-(2-phenylethyl)-1-β-D-arabinofuranosylcytosine,
5-(4-phenylbut-1-yl)-1-β-D-arabinofuranosylcytosine,
5-(4-hydroxybut-1-yl)-1-β-D-arabinofuranosylcytosine,
5-(5-hydroxy-2-methylpent-1-yl)-1-β-D-arabinofuranosylcytosine
5-(3-oxobut-1-yl)-1-β-D-arabinofuranosylcytosine,
5-(2-methyl-4-oxohept-1-yl)-1-β-D-arabinofuranosylcytosine,
5-[2-methyl-3-(N,N-dimethylamido)prop-1-yl]-1-β-D-arabinofuranosylcytosine,
5-[4-(N,N-dibutylamido)but-1-yl]-1-β-D-arabinofuranosylcytosine,
5-(3,3,3-trifluoroprop-1-yl)-1-β-D-arabinofuranosylcytosine, and
5-(4,4,4-trifluorobut-1-yl)-1-β-D-arabinofuranosylcytosine.

The following example refers to Reaction (3).

EXAMPLE XIII

5-(1-Hydroxy) substituted cytosine nucleosides 5-(1-Methoxyprop-1-yl)cytidine (315 mg, 1 mmol) in 10 ml 0.05 N HCl is stirred for approximately 48 hours at about 30° C. Column chromatography of the reaction mixture on molecular exclusion resin eluting with water affords 5-(1-methoxyprop-1-yl)cytidine and 5-(1-hydroxyprop-1-yl)cytidine.

Repeating the procedure on compounds of formula (IB) recited in Examples II–VIII is productive of the corresponding 5-(1-hydroxy) substituted cytosine nucleosides of formula (ID).

Examples XIV–XVII refer to Reaction (4).

EXAMPLE XIV

5-(Prop-2-en-1-yl)cytidine

5-Chloromercuricytidine (1.22 g, 2.55 mmol) is stirred in 40 ml methanol, and $CuCl_2$ (410 mg, 3.1 mmol), allyl chloride (2.2 ml, 27 mmol) and 6.0 ml of 0.1 N $Li_2PdCl_4$ in methanol are added consecutively. Thereafter, stirring is continued at room temperature. After about 12 hours the reaction mixture is treated for about one minute with hydrogen sulfide and filtered to afford a yellow colored methanolic solution. Evaporation of the filtrate to near dryness and column chromatography on silica gel eluting with a methanol/chloroform gradient affords a white crystalline solid after concentration. Recrystallization from water or acetonitrile yields analytically pure white crystals of 5-(prop-2-en-1-yl)cytidine; m.p. 176° C., (decomposes); $^1H$ NMR ($D_2O$) $\delta 7.8$ (s,1), 6.0 (broad m, 1), 5.92 (narrow m, 1), 5.20 (dm, 1, J=10 Hz), 5.12 (dm, 1, J=18 Hz), 4.2 (complex m, 3), 3.88 (narrow m, 2), 3.11 (d, 2, J=6 Hz); UV $\lambda_{max}^{H2O}$ 278 nm ($\epsilon 8100$), $\lambda_{min}^{H2O}$ 254 ($\epsilon 5100$).

Analysis calculated for $C_{12}H_{17}N_3O_5$: C, 50.88; H, 6.05; N 14.83; found, C, 50.97; H, 5.71; N 14.65.

EXAMPLE XV

Repeating the procedure of Example XIV, but replacing allyl chloride with:
3-chloro-1-butene,
3-acetoxy-2-methyl-1-pentene,
3-hydroxy-4-methyl-1-pentene or
3-hydroxy-2-methyl-1-hexene
is productive of the following C-5 substituted cytidines of formula (IE), i.e.
5-but-2-en-1-yl)cytidine,
5-(2-methylpent-2-en-1-yl)cytidine,
5-(4-methylpent-2-en-1-yl)cytidine and
5-(2-methylhex-2-3n-1-yl)cytidine.

EXAMPLE XVI

Repeating the procedures of Examples XIV and XV, but replacing 5-chloromercuricytidine with 5-chloromercuri-2'-deoxycytidine is productive of the following 5-substituted 2'-deoxycytidines of formula (IE), i.e.,
5-(prop-2-en-1-yl)-2'-deoxycytidine,
5-(but-2-en-1-yl)-2'-deoxycytidine,
5-(2-methylpent-2-en-1-yl)-2'-deoxycytidine,
5-(4-methylpent-2-en-1-yl)-2'-deoxycytidine and
5-(2-methylhex-2-en-1-yl)-2'-deoxycytidine.

EXAMPLE XVII

Repeating the procedures of Examples XIV and XV, but replacing 5-chloromercuricytidine with 5-chloromercuri-1-$\beta$-D-arabinofuranosylcytosine is productive of the following C-5 substituted 1-$\beta$-D-arabinofuranosylcytosines of formula (IE), i.e.
5-(prop-2-en-1-yl)-1-$\beta$-D-arabinofuranosylcytosine,
5-(but-2-en-1-yl)-1-$\beta$-D-arabinofuranosylcytosine,
5-(2-methylpent-2-en-1-yl)-1-$\beta$-D-arabinofuranosylcytosine,
5-(4-methylpent-2-en-1-yl)-1-$\beta$-D-arabinofuranosylcytosine and
5-(2-methylhex-2-en-1-yl)-1-$\beta$-D-arabinofuranosylcytosine.

EXAMPLE XVIII

The acid addition salts of the subject compounds of the present invention can be readily obtained by lyophilization of a desired acid solution containing a specific compound. For example, 5-(propen-1-yl)cytidine (280 mg, 1.0 mmol) is suspended in distilled water with stirring, and 1.05 ml of 1.0 N HCl is added slowly. The HCl salt of 5-(propen-1-yl)cytidine is recovered by lyophilization.

Other acid addition salts of the invention may be similarly prepared.

What is claimed is:

1. A compound of the formula

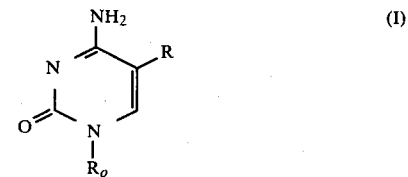

wherein $R_o$ is $\beta$-D-ribofuranosyl, $\beta$-D-2-deoxyribofuranosyl or $\beta$-D-arabinofuranosyl and R is selected from the group consisting of

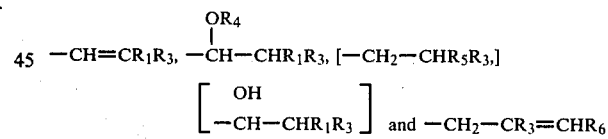

wherein $R_1$ is hydrogen; $R_3$ is hydrogen or methyl; $R_4$ is $C_{1-4}$ lower alkyl; $R_6$ is hydrogen; and the pharmaceutically acceptable acid addition salts thereof.

2. A compound according to claim 1 wherein $R_o$ is $\beta$-D-2-deoxyribofuranosyl.

3. A compound according to claim 2 wherein $R_3$ is hydrogen.

4. The compound of claim 2 which is 5-(ethenyl)-2'-deoxycytidine.

5. A compound according to claim 2, wherein R is allyl.

6. A compound according to claim 2, wherein R is 1-methoxyethyl.

7. A method of treating herpes simplex virus 1 in a host mammal afflicted with such infection which comprises administering to said host an effective amount of a compound according to claims 2, 3, 4, 5 or 5.

* * * * *